United States Patent
Rauch

(10) Patent No.: US 8,731,262 B2
(45) Date of Patent: May 20, 2014

(54) MEDICAL IMAGE AND VESSEL CHARACTERISTIC DATA PROCESSING SYSTEM

(75) Inventor: John Christopher Rauch, Warwick, RI (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 474 days.

(21) Appl. No.: 13/026,417

(22) Filed: Feb. 14, 2011

(65) Prior Publication Data

US 2011/0299749 A1 Dec. 8, 2011

Related U.S. Application Data

(60) Provisional application No. 61/350,944, filed on Jun. 3, 2010.

(51) Int. Cl.
*G06K 9/00* (2006.01)

(52) U.S. Cl.
USPC .......................................... 382/130

(58) Field of Classification Search
CPC ................... A61B 6/504; G06T 2207/30104
USPC .......................................... 382/130
See application file for complete search history.

(56) References Cited

U.S. PATENT DOCUMENTS

| | | | |
|---|---|---|---|
| 6,052,476 A * | 4/2000 | Qian et al. | 382/130 |
| 7,403,810 B2 | 7/2008 | Li | |
| 7,519,412 B2 | 4/2009 | Mistretta | |
| 7,545,901 B2 | 6/2009 | Mistretta | |
| 7,702,138 B2 * | 4/2010 | Lienard et al. | 382/128 |
| 7,715,519 B2 * | 5/2010 | Tsukagoshi et al. | 378/4 |
| 8,116,844 B2 * | 2/2012 | Schmidt | 600/420 |
| 8,300,912 B2 * | 10/2012 | Sanada et al. | 382/132 |
| 2007/0009080 A1 | 1/2007 | Mistretta | |
| 2008/0009698 A1 | 1/2008 | Boese | |
| 2008/0051648 A1 * | 2/2008 | Suri et al. | 600/407 |
| 2008/0247503 A1 | 10/2008 | Lauritsch | |
| 2008/0317323 A1 | 12/2008 | Kinnstatter et al. | |
| 2009/0016587 A1 | 1/2009 | Strobel | |
| 2009/0090873 A1 | 4/2009 | Sapp et al. | |
| 2009/0110252 A1 * | 4/2009 | Baumgart et al. | 382/130 |
| 2009/0297004 A1 | 12/2009 | Baumgart | |
| 2010/0034446 A1 | 2/2010 | Zhu et al. | |
| 2010/0053209 A1 | 3/2010 | Rauch | |
| 2010/0259550 A1 | 10/2010 | Baumgart et al. | |

FOREIGN PATENT DOCUMENTS

DE 102007028226 12/2008
DE 102009024765 12/2010

* cited by examiner

*Primary Examiner* — Matthew Bella
*Assistant Examiner* — Dennis Rosario
(74) *Attorney, Agent, or Firm* — Brennan K Bradley

(57) ABSTRACT

An image data processing system automatically indicates an image of a digitally subtracted Angiography (DSA) image sequence is associated with at least one of, arterial, venous, or capillary phases of blood flow. The system includes an interface for acquiring data representing a DSA sequence of digitally subtracted images enhancing vessel structure. An image data processor automatically indicates an image of the DSA sequence is associated with at least one of, arterial, venous, or capillary phases of blood flow by determining individual minimum luminance intensity level values of individual images of the DSA sequence and using the determined individual minimum luminance intensity level values in identifying images of the DSA sequence are associated with at least one of, arterial, venous, or capillary phases of blood flow. An output processor automatically assigns an attribute to image data to identify vessel phase in response to the identifying images of the DSA sequence.

34 Claims, 17 Drawing Sheets

Figure 15 Composite Image of Vessel Phases

MEDICAL IMAGE AND VESSEL CHARACTERISTIC DATA PROCESSING SYSTEM

This is a non-provisional application of provisional application Ser. No. 61/350,944 filed Jun. 3, 2010, by J. C. Rauch.

FIELD OF THE INVENTION

This invention concerns an image data processing system for automatically indicating an image of a Digitally Subtracted Angiography (DSA) image sequence is associated with at least one of arterial, venous, or capillary phases of blood flow.

BACKGROUND OF THE INVENTION

In diagnostic imaging it is desirable to be able to examine phases of blood flow to look for abnormalities. The ability to individually look at arterial, capillary, and venous phases simplifies a diagnosis and treatment workflow and produces improved consistency. There are some procedures in which it is advantageous to be able to visualize either the arteries or the veins independently of one another, as some ailments primarily affect either arteries or veins. It is also desirable to be able to visualize both the arteries and veins simultaneously, but with the arteries and veins depicted differently (e.g. in different colors). This is especially helpful when interactions between arteries and veins are of interest; for example in diagnosing, evaluating, or treating Arterial Venous Malformations (AVMs) or fistulae.

In known angiography systems a user manually selects image frames of interest and manually generates composite images of arterial or venous frames. A user is responsible for identifying the vessel phases of each image frame which is a burdensome and time consuming task. A system according to invention principles addresses these requirements and associated problems.

SUMMARY OF THE INVENTION

A system enables the detection of vascular phases (arterial, capillary, and venous) of patient anatomy in a time varying X-ray image clip capturing a contrast bolus injection. An image data processing system automatically indicates an image of a digitally subtracted Angiography (DSA) image sequence is associated with at least one of, arterial, venous, or capillary phases of blood flow. The system includes an interface for acquiring a sequence of images of patient vessels both prior to and following introduction of contrast agent into the vessels and subtracting a mask image representing background detail in the absence of a contrast agent to produce data representing a DSA sequence of digitally subtracted images enhancing vessel structure. An image data processor automatically indicates an image of the DSA sequence is associated with at least one of, arterial, venous, or capillary phases of blood flow by determining individual minimum luminance intensity level values of individual images of the DSA sequence and using the determined individual minimum luminance intensity level values in identifying images of the DSA sequence are associated with at least one of, arterial, venous, or capillary phases of blood flow. An output processor automatically assigns an attribute to image data to identify vessel phase in response to the identifying images of the DSA sequence.

DETAILED DESCRIPTION OF THE INVENTION

A system provides automatic detection and classification of the vessels as arteries, veins, and capillaries within a DSA image sequence and displays classified vessels, in response to a contrast agent bolus injection into a patient. The system identifies different phases of blood flow depicted by flow of contrast agent in patient anatomy X-ray images. Blood flow phases in the tissues of the body include arterial, capillary, and venous phases. In the capillary phase contrast agent is located almost entirely in the capillaries, within the tissue itself. In the arterial and venous phases, the contrast agent is located in the vessels supplying (arteries) blood to the tissue or draining (veins) blood from the tissue. The system automatically identifies, Arterial phase (start and end), Capillary phase (start, maximum blush, and end) and Venous phase (start and end). The system analyzes the change in image luminance intensity values over time to identify frames that specifically capture contrast agent as it moves through arteries, capillaries, and veins.

The system automatically detects different vessel phases and automates image processing, analysis, and display of images without need for user interaction. The system generates a composite image of either the arterial or venous system from an X-ray image sequence to be used as a mask image for subsequent fluoroscopy and selects specific images for analysis and display. The system selects an appropriate color for individual particular time durations within the duration of an image sequence and maps color to particular images of the sequence to generate colorized flow images indicating different vessel blood flow phases. The system also sets boundaries for image looping (e.g. boundaries enabling looping through a sequence of arterial image frames in a video clip, for example). The system analyzes diagnostic subtracted angiographic images to provide image frames showing contrast agent in an arterial phase, for example, since arterial phase images have larger numbers of pixels with relatively darker than background luminance intensity values. In a capillary phase, image frames with contrast agent are distinguished since they a have larger numbers of pixels (in comparison to pixel counts in the arterial or venous phases) with only slightly darker than background luminance intensity values. In a venous phase, image frames with contrast agent are distinguished since they have larger numbers of pixels with significantly darker than background luminance intensity values (though may not be as dark as in the arterial flow frames as the veins may drain multiple arteries which dilutes the contrast in those veins).

Figure 1:
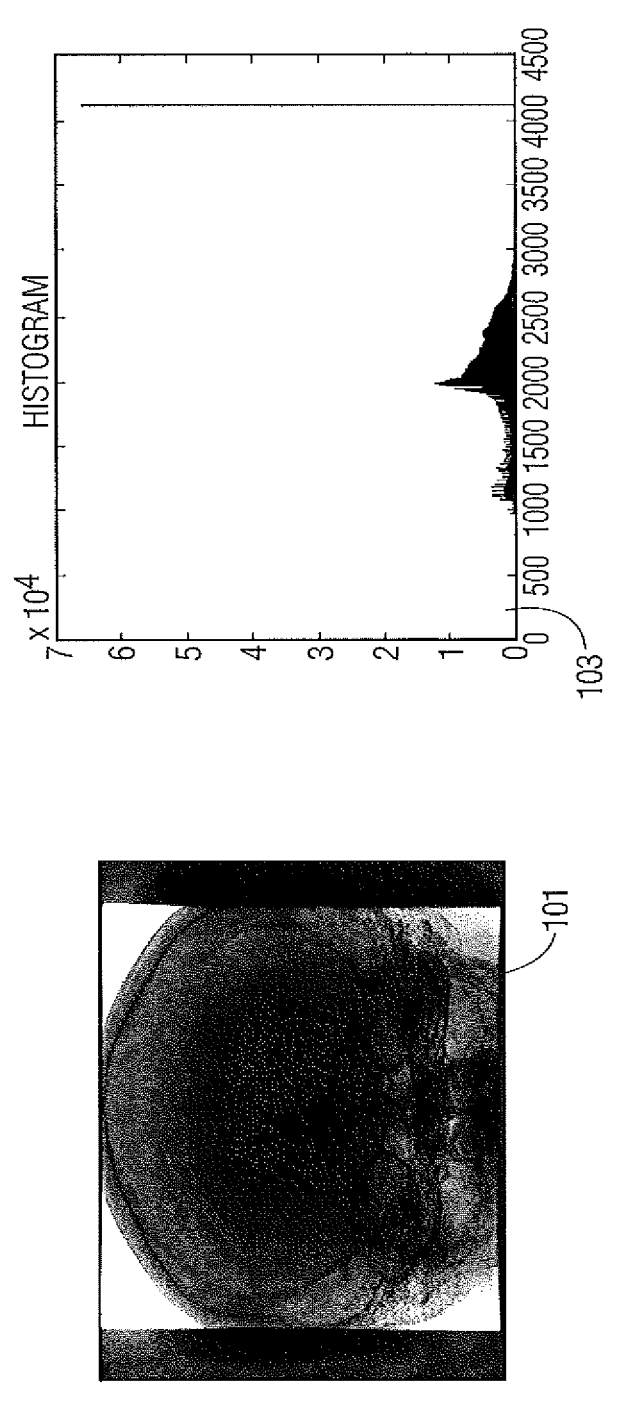
FIG. 1 shows an example X-ray image and associated histogram.

A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast). FIG. 1 shows an example X-ray image 101 and associated histogram 103 provided by the system. In image 101, a large number of pixels do not pass through the object and are fully saturated (i.e. have maximum intensity value) causing the spike to the right of the Histogram 103.

Figure 2:
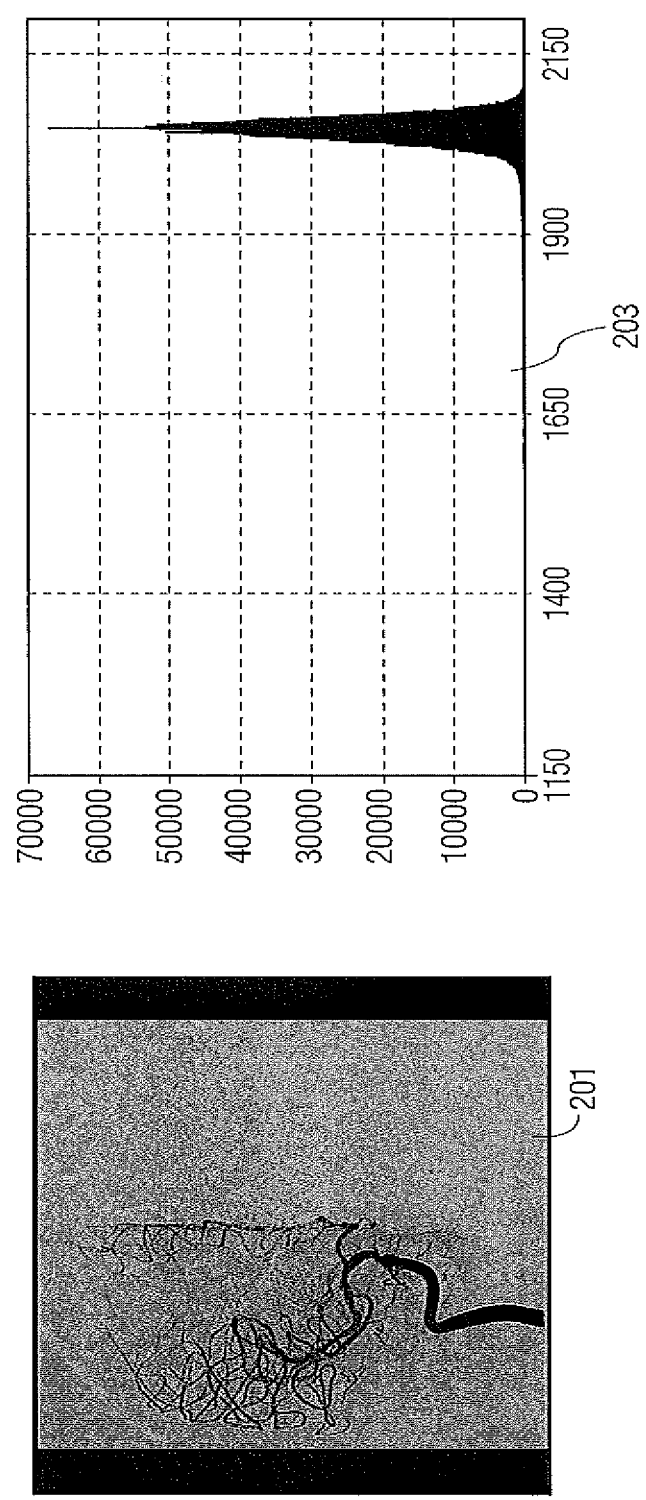
FIG. 2 show a DSA image of the right internal carotid artery with an intra-arterial injection of Iodine contrast and an associated histogram of the DSA image.

Digital Subtraction Angiography (DSA) highlights contrast enhanced features visible in images of a sequence of images of an object. An image (a mask image) of the object is acquired in the absence of contrast agent. A subtraction is performed between the mask image and each subsequent image of the sequence acquired in the presence of contrast agent. If there is no movement of the object during acquisition of the sequence, a nearly perfect subtraction is achieved and produces a gray image. Contrast agent is routinely introduced into vessels during DSA image acquisition to visualize the vessels. A positive contrast agent has a density greater than blood and tissue and a negative contrast agent has a density less than blood and tissue. A positive contrast agent is contrast agent that is denser than the surrounding blood or tissues: Iodine, Barium, and Gadolinium are examples of a positive contrast agent. Positive contrast agent is visible in the image as darker (lower intensity) pixels. A negative contrast agent is contrast agent that is less dense than the surrounding blood or tissues, air, Oxygen, and $CO_2$ are examples of negative contrast agent. A negative contrast agent is visible in the image as lighter (higher luminance intensity) pixels. FIG. 2 show a DSA image 201 of the right internal carotid artery with an intra-arterial injection of Iodine contrast and an associated histogram 203 of the DSA image plotting number of pixels (on the y-axis) in the image having a specific luminance intensity value (x-axis).

Figure 6:
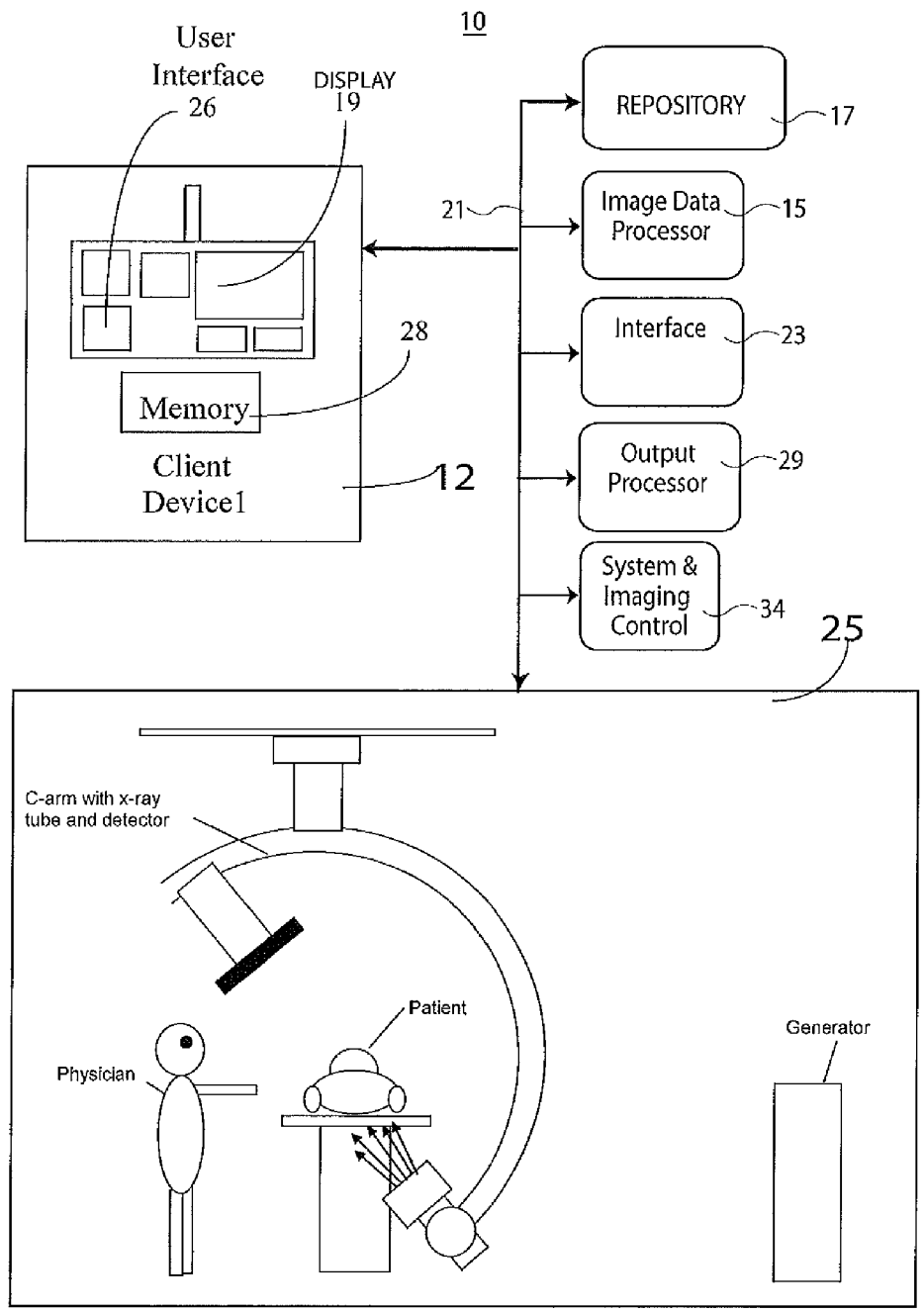
FIG. 6 shows an image data processing system for automatically indicating an image of a digitally subtracted Angiography (DSA) image sequence is associated with at least one of, arterial, venous, or capillary phases of blood flow, according to invention principles.

FIG. 6 shows image data processing system 10 for automatically indicating an image of a digitally subtracted Angiography (DSA) image sequence is associated with at least one of arterial, venous, or capillary phases of blood flow. System 10 includes one or more processing devices (e.g., workstations, computers or portable devices such as notebooks, Personal Digital Assistants, phones) 12 that individually include a user interface 26 enabling user interaction with a Graphical User Interface (GUI) and display 19 supporting GUI and medical image presentation in response to predetermined user (e.g., physician) specific preferences. System 10 also includes at least one repository 17, image data processor 15, interface 23, output processor 29, imaging devices 25 and system and imaging control unit 34. System and imaging control unit 34 controls operation of one or more imaging devices 25 for performing image acquisition of patient anatomy in response to user command. Imaging devices 25 may comprise a single device (e.g., a mono-plane or biplane X-ray imaging system) or multiple imaging devices such as an X-ray imaging system together with a CT scan, MRI device or Ultrasound system, for example). The units of system 10 intercommunicate via network 21. At least one repository 17 stores medical image studies for patients in DICOM compatible (or other) data format. A medical image study individually includes multiple image series of a patient anatomical portion which in turn individually include multiple images.

Image data processing system 10 automatically indicates an image of a digitally subtracted Angiography (DSA) image sequence is associated with at least one of, arterial, venous, or capillary phases of blood flow. Interface 23 acquires a sequence of images of patient vessels both prior to and following introduction of contrast agent into the vessels and subtracts a mask image representing background detail in the absence of a contrast agent to produce data representing a DSA sequence of digitally subtracted images enhancing vessel structure. Image data processor 15 automatically indicates an image of the DSA sequence is associated with at least one of arterial, venous, or capillary phases of blood flow by determining individual minimum luminance intensity level values of individual images of the DSA sequence. Image data processor 15 uses the determined individual minimum luminance intensity level values in identifying images of the DSA sequence are associated with at least one of, arterial, venous, or capillary phases of blood flow. Output processor 29 automatically assigns an attribute to image data to identify vessel phase associated with individual images of the identified images of the DSA sequence One or more imaging devices 25 acquires multiple DSA sequential images (which may or may not be synchronized with ECG and respiratory signals) of a vessel structure in the presence of a contrast agent in a 3D volume interest. At least one repository 17 stores 2D image data representing a 2D DSA X-ray image sequence through the imaging volume in the presence of a contrast agent. Image data processor 15 uses image sequence data comprising 3D image data or 2D image data in deriving blood flow related information for the vessels. The system 10 vessel phase detection processes a contrast enhanced DSA image sequence encompassing an image indicating introduction of a contrast agent bolus of known type, and am image indicating maximum capillary blush where most of the contrast is in the capillaries in the image. The contrast agent bolus is a finite but contiguous bolus (does not stop and re-start), of shorter duration than the time required for the contrast agent to travel from the arteries to the capillaries in the area being imaged. Further, patient or patient support table movement is restricted to be negligible during the image acquisition.

System 10 provides vessel phase detection with both intra-arterial and intra-venous contrast agent. The system is described in the context of use of a positive contrast agent, as angiographic procedures most commonly use a positive contrast agent for DSA imaging. However, the system is also usable with a negative contrast agent. During a typical diagnostic or therapeutic interventional procedure, a contrast agent is introduced into a particular artery via a micro-catheter, sheath, or other hollow lumen intravascular navigation device. The result is that contrast agent is present only in the arteries, capillaries, and veins that are connected to the artery into which the contrast was introduced highlighting the vessels of interest.

Alternatively, contrast agent may be directly introduced into a vein via simple needle access intra-venous injection. The contrast agent flows from the vein to the heart, to the lungs, back to the heart, and then out to the rest of the body. This journey ensures a thorough mixing and even distribution of the contrast agent. However, contrast agent introduced into a vein typically requires more contrast to image an area than an intra-arterial contrast injection, as the contrast agent enhanced blood is present in the whole body. Imaging of an intra-vascular contrast injection can produce images of the entire vasculature including arteries, capillaries, and veins. However this requires more complicated acquisition timing to capture the entrance of the contrast agent bolus into the area being imaged.

Figure 3:
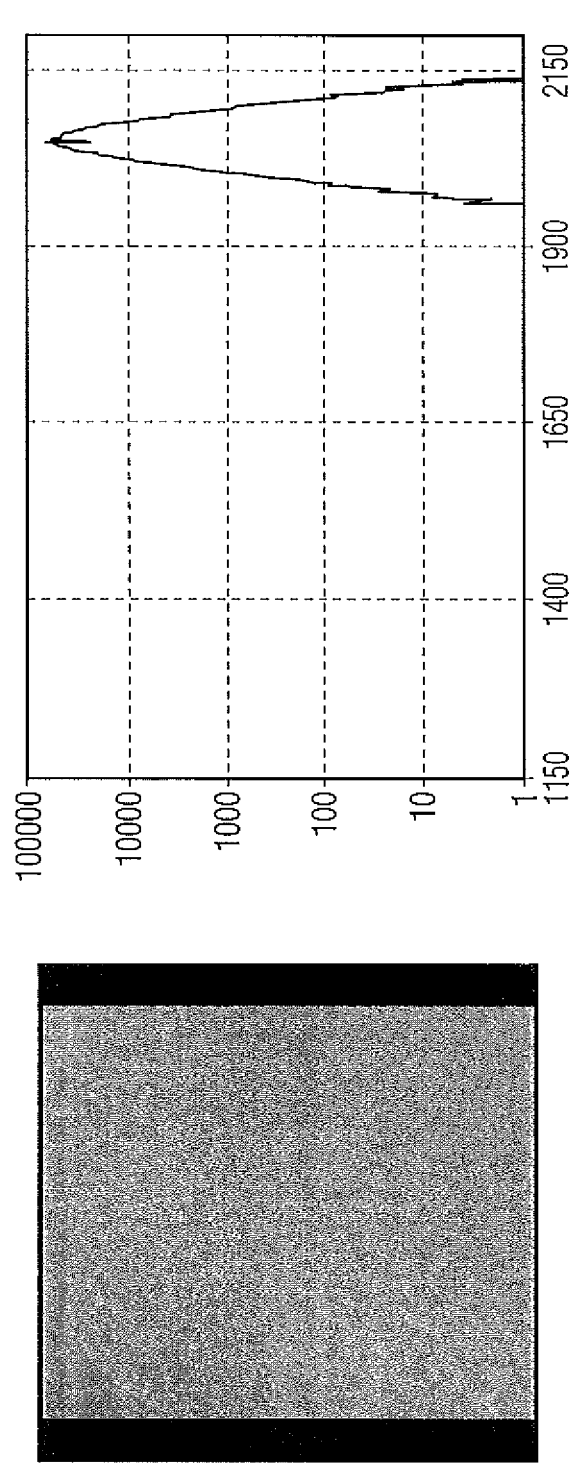
FIG. 3 shows a pre-fill phase DSA image and associated histogram, according to invention principles.

Images acquired before the introduction of a contrast agent bolus belong to a pre-fill phase. A DSA image of the pre-fill phase shows little, and in the situation of perfect subtraction with no noise would be a uniform image of one intensity value. In practice, this is only observed when viewing a DSA image of the mask frame. In other DSA images of the pre-fill phase, there is some variation in luminance intensity values among the pixels due to slight patient movement, noise, and other effects. The result is that these images are composed of luminance intensity values that mimic a Gaussian distribution about the perfect subtraction intensity value. FIG. 3 shows a pre-fill phase DSA image and associated histogram with a logarithmic vertical axis indicating number of pixels (y-axis) versus luminance intensity value (x-axis).

Figure 4:
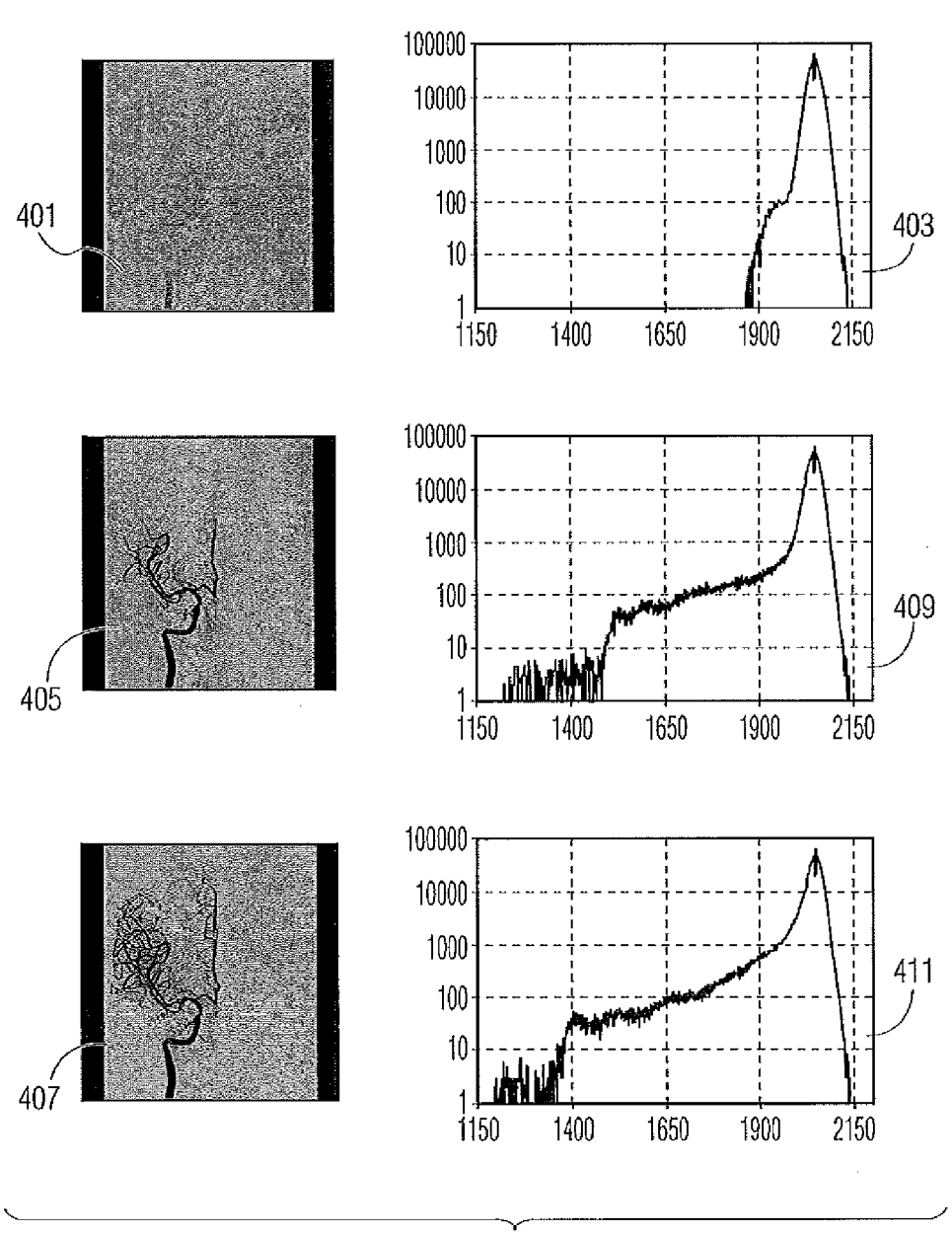
FIG. 4 shows contrast agent flow into arteries making the arteries become visible and associated corresponding histograms, according to invention principles.

As contrast agent flows into the arteries present in the area of the object being imaged, the arteries become visible. FIG. 4 shows contrast agent flow into arteries in image 401 making the arteries become visible and an associated corresponding histogram 403 with a logarithmic vertical axis indicating the number of pixels having a particular intensity value (y-axis) versus the available luminance intensity values (x-axis). As contrast agent flows, as illustrated in images 405 and 407, the corresponding associated histograms 409 and 411 change. A more dense contrast agent medium is used, which causes increased X-ray attenuation and a dark depiction of the vessels. The darker pixels are lower luminance intensity pixels and result in the spreading of the histogram toward lower intensity values as illustrated in histograms 409 and 411. In the case of a negative contrast agent medium the vessels appear lighter and the histogram spreads toward higher intensity values. The size of vessel is related to the luminance intensity values detected for that vessel. The larger vessels hold more contrast agent per unit length than smaller vessels and appear darker. Another factor that influences the luminance intensity of a vessel is the directionality of the vessel. A vessel that is parallel to the imaging plate is fully displayed in the image, but a vessel that is perpendicular to the imaging plate show a cross-sectional area in the image. For vessels of equivalent size and length, the luminance intensities displayed for a perpendicular vessel, in the cross-sectional area, are darker than the intensities displayed for a parallel vessel, where perpendicular and parallel are determined in reference to the imaging plate. This is due to the fact that there is more volume of contrast agent medium per display area in the case of a perpendicular vessel. Therefore, luminance intensities that represent the arteries in the image have a range of values that extend away from the intensities that comprise the pre-fill phase images.

Figure 5:
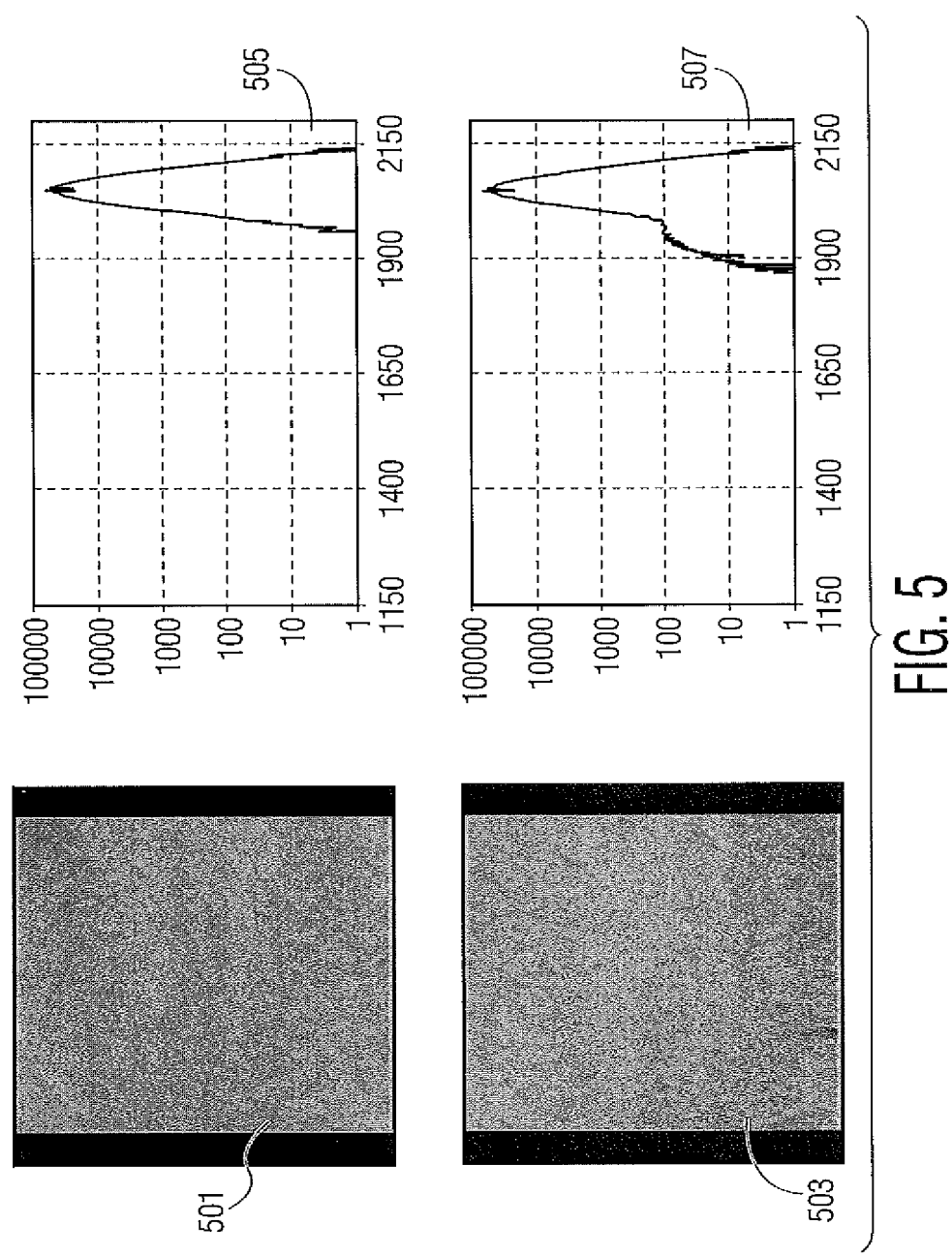
FIG. 5 illustrates detection of the start of the arterial phase as a first image in an image sequence having a histogram containing luminance intensities outside the range of intensities for the pre-fill phase, according to invention principles.

FIG. 5 illustrates detection of the start of the arterial phase as a first image in an image sequence having a histogram containing luminance intensities outside the range of intensities for the pre-fill phase. Images 503 and 501 are sequential images. Image 503 shows appearance of arteries and start of the arterial phase as indicated in histogram 507 indicating number of pixels (y-axis) versus luminance intensity value (x-axis) and containing luminance intensities outside the range of intensities for the pre-fill phase. The pre-fill phase for comparison is shown in image 501 and associated histogram 505.

As the contrast begins to flow out of the arteries and into the capillaries, there is an increase in the number of pixels having luminance intensities closer to the intensities of the pre-fill phase images and a decrease in the number of pixels having darker intensities. The reason for this is that the contrast is flowing into increasingly smaller vessels, and the intensity of these smaller vessels is higher than the intensities of the larger vessels because there is less blood (and contrast) per unit length of vessel. There is a limit to this process and this is the capillaries themselves. The capillaries are the vessels that supply blood to the tissues, and are the smallest vessels in the body. The capillaries by necessity are quite numerous, in order to supply the whole volume of a tissue with blood and are depicted in a DSA image by a more moderate change in the intensity value than observed for the arteries, and the change in luminance intensity in the capillaries is commonly termed a capillary blush. The large numbers of capillaries means that while the intensity values are higher, the number of pixels having these intensities is greater.

DSA images with contrast agent are typically acquired so that the contrast agent injection is terminated before the majority of visible contrast agent reaches the capillaries. This allows for more distinct visualization of the capillaries, with one or more images representing the maximum capillary blush corresponding to most of the contrast being in the capillaries. The blood flow process works in reverse as the contrast agent flows from the capillaries into the veins. The number of pixels with luminance intensities near the range of pre-fill phase intensities begins to diminish as the contrast agent flows out of the capillaries and the number of pixels having lower intensity values increases as the contrast flows into the veins. As the contrast agent enhanced blood flows through the veins and out of the image area, the number of lower intensity values decreases.

Figure 7:
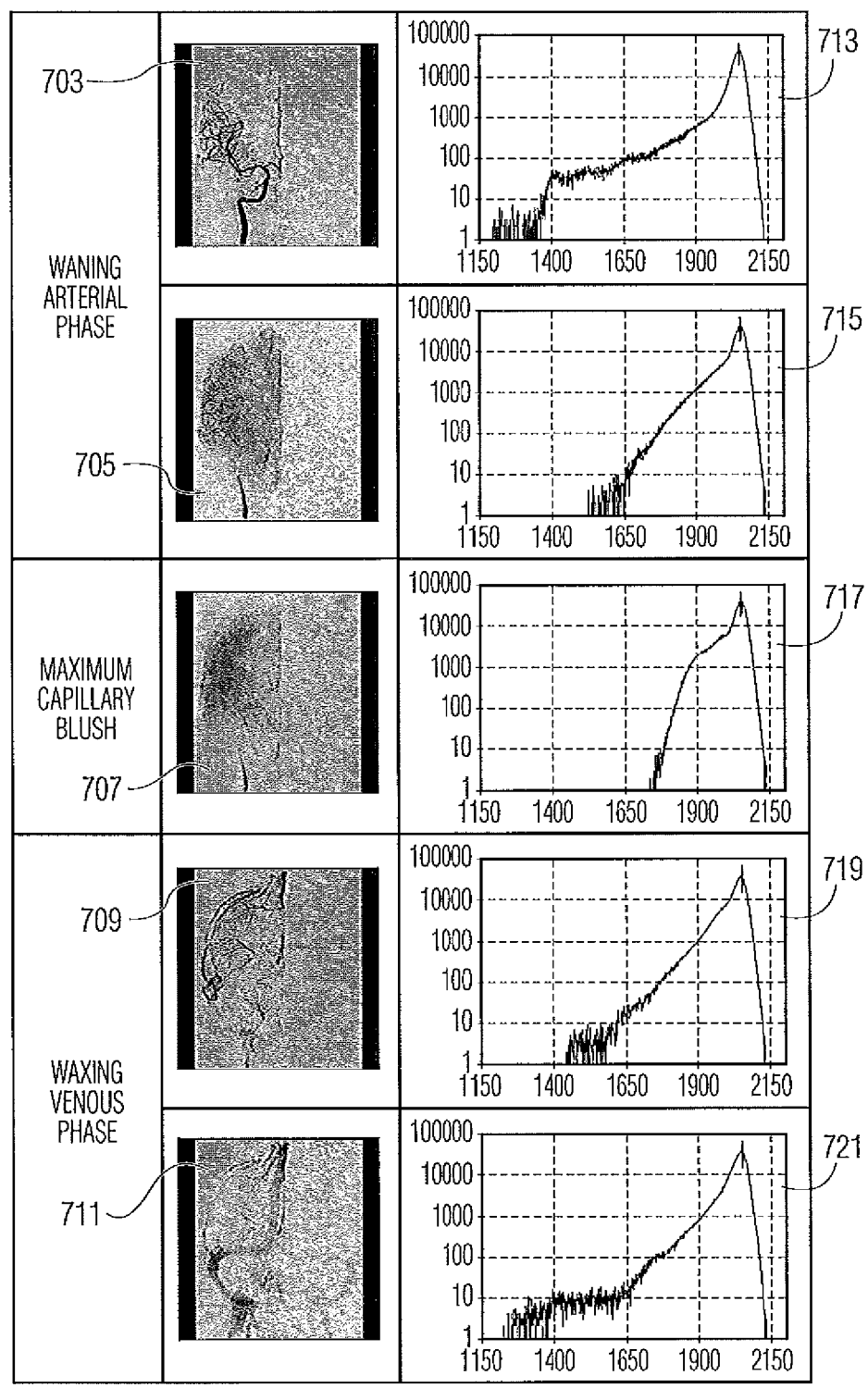
FIG. 7 illustrates contrast agent flow out of the arteries, maximum capillary blush and increasing flow into venous vessels.

FIG. 7 shows images indicating contrast agent flow out of the arteries, maximum capillary blush and increasing flow into venous vessels. Images 703 and 705 (and corresponding histograms 713 and 715), show contrast agent flow out of the arteries and into the capillaries. Image 707 shows an image of maximum capillary blush and corresponding histogram 717 showing an increasing number of pixels having luminance intensities closer to the intensities of the pre-fill phase images and a decrease in the number of pixels having darker intensities. Images 709 and 711 (and corresponding histograms 719 and 721), show increasing contrast agent flow into venous vessels.

System 10 employs multiple different methods to locate an image in an image sequence containing the maximum capillary blush. In one embodiment system 10 identifies an image in the sequence containing the maximum capillary blush after the start of the arterial phase having a minimum luminance intensity value higher than both preceding and following images in the sequence. Alternatively (or in addition) system 10 identifies an image in the sequence containing the maximum capillary blush as having the maximum number of pixels in the capillary luminance intensity range (i.e. adjacent to, but not including, the pre-fill phase luminance intensity range).

Figure 8:
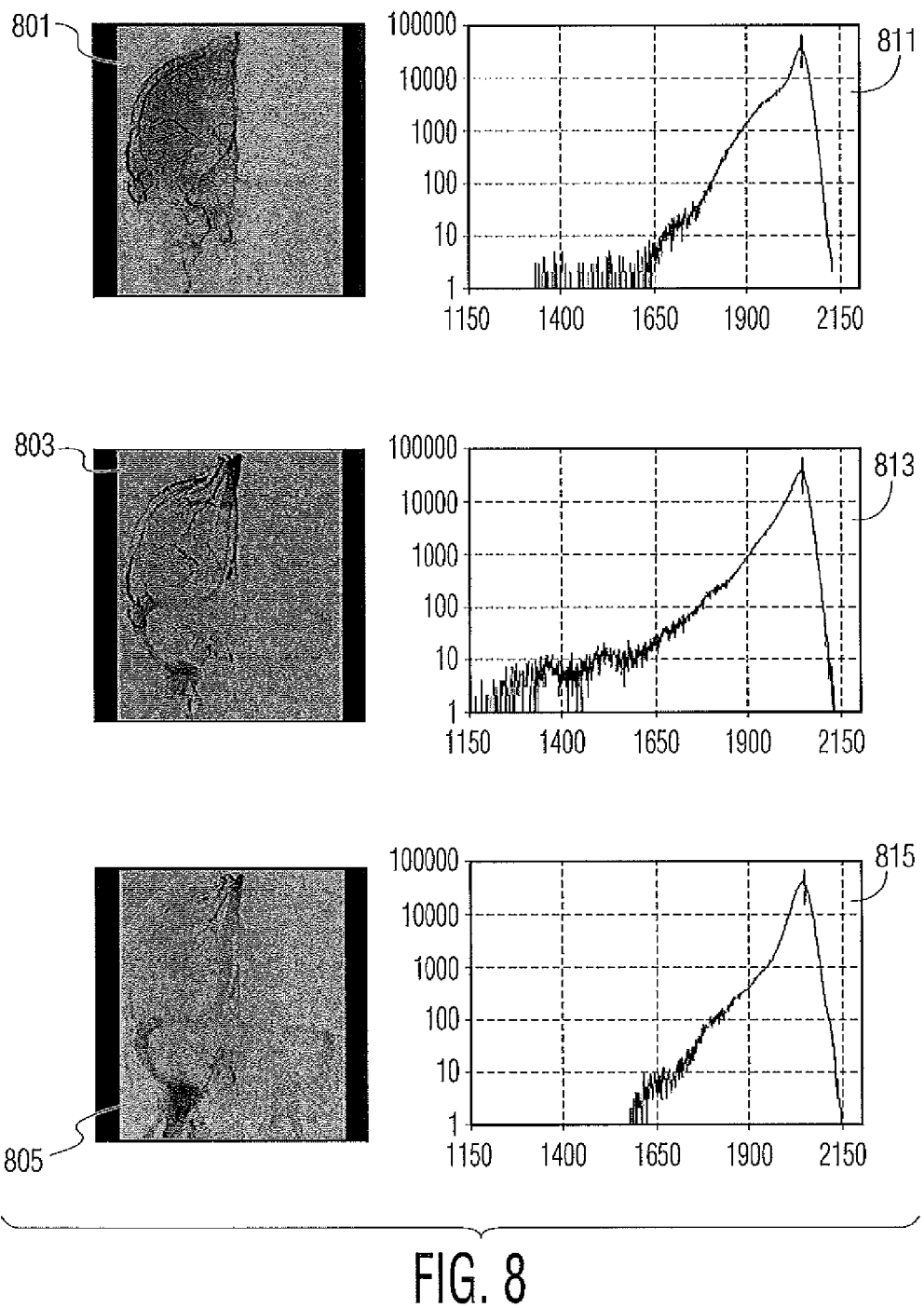
FIG. 8 illustrates venous phase flow and associated histograms, according to invention principles.

FIG. 8 illustrates venous phase flow and associated histograms. The venous phase operates similarly to the arterial phase in reverse. Images 801, 803 and 805 show the flow of contrast agent through the veins: flow entering the smaller veins in image 801, flow leaving the smaller veins and entering the larger veins in image 803, and flow leaving the larger veins in image 805 with corresponding histograms 811, 813 and 815. As the contrast agent flows out of the capillaries and into the smaller veins, the veins become visible and have increasingly darker luminance intensities than the capillaries. Eventually the contrast agent leaves the capillaries completely and begins to flow out of the veins and the image area entirely. When the contrast agent has left the image area, the histogram of the image and its histogram resemble those of the pre-fill phase images.

Figure 9:
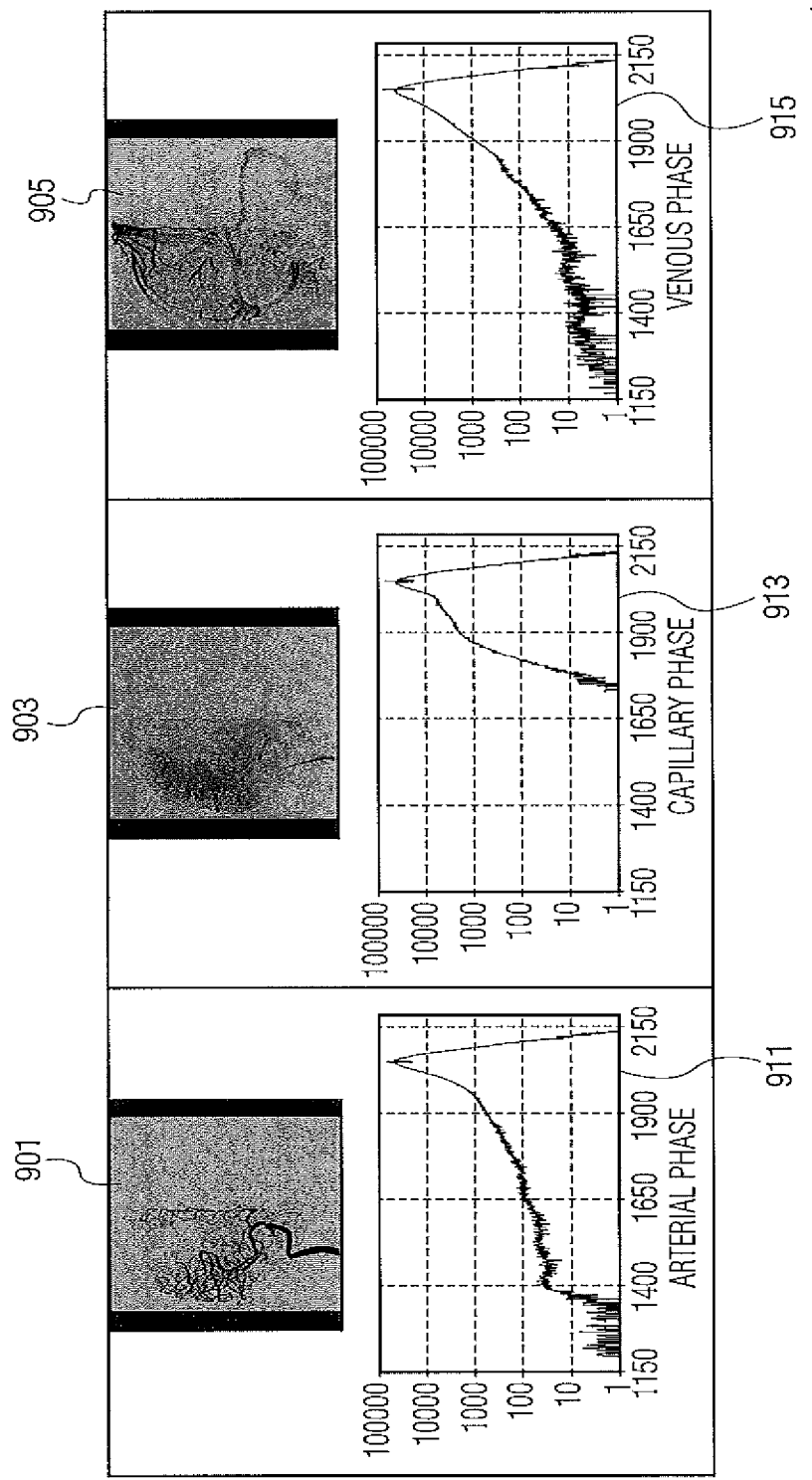
FIG. 9 illustrates histogram plots of minimum intensity values of arterial, capillary and venous phases, according to invention principles.

FIG. 9 illustrates histogram plots of images showing arterial, capillary and venous phases. Images 901, 903 and 905 comprise images of an anatomical portion indicating arterial, capillary and venous blood flow phases respectively and histograms 911, 913 and 915 show corresponding histograms indicating number of pixels (logarithmic y-axis) in the images having particular luminance intensity values (x-axis) for the arterial, capillary and venous phase images. In examining multiple images of a DSA image sequence, parameters of the histograms of the DSA images change as the blood flows through the vasculature, into and out of the image area. Images 901, 903 and 905 and histograms 911, 913 and 915 indicate substantial difference between image 903 (and histogram 913) of the capillary phase image and the images and histograms of the arterial and venous phases. Specifically, the minimum luminance intensity value in capillary image 903 is substantially different from arterial and venous images 901 and 905.

The minimum luminance intensity value is the lowest intensity value that occurs in the image. In the arterial phase, image 901 and histogram 911, the minimum luminance intensity value is substantially lower than that of the pre-fill images. The minimum luminance intensity value increases as the contrasted blood flows out of the arteries and into the capillaries, image 903 and histogram 913. As the contrasted blood flows out of the capillaries and into the veins, the minimum luminance intensity value again decreases until the veins are maximally filled with contrast, image 905 and histogram 915. As contrast flows out of the veins and out of the image area, the minimum luminance intensity value again increases to the value of the pre-fill images.

Figure 10:
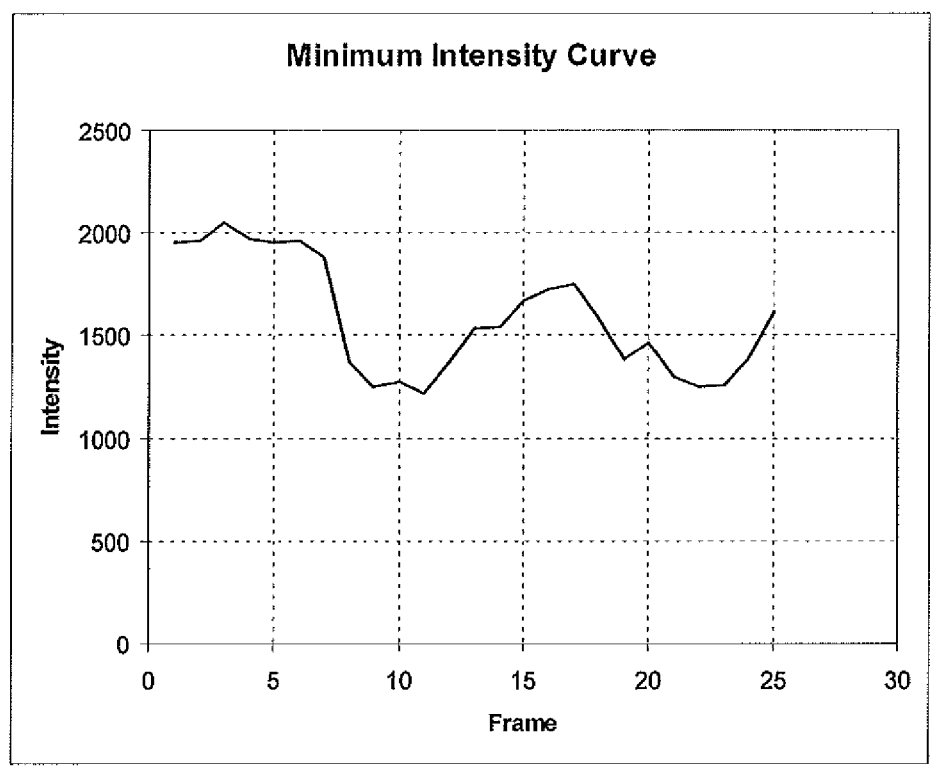
FIG. 10 illustrate a plot of minimum luminance intensity value for each frame of a sequence, according to invention principles.

FIG. 10 illustrate a plot of minimum luminance intensity value (y-axis) for each frame (numbered on x-axis) of a sequence. In this case, frame 3 is a mask frame (representing background detail in the absence of a contrast agent) and has a higher minimum luminance intensity value than other frames. As contrast agent enters the image (in frame 7), the minimum luminance intensity begins to reduce, reaching a minimum and rising as the majority of the contrast agent flows out of the arteries. The minimum luminance intensity reaches a maximum when the majority of the contrast agent is in the capillaries and then falls again as the contrast agent enters the veins. When the majority of the contrast agent is in the veins another minimum is obtained. The minimum intensity curve rises as the contrast agent leaves the veins and the image area altogether.

Figure 11:
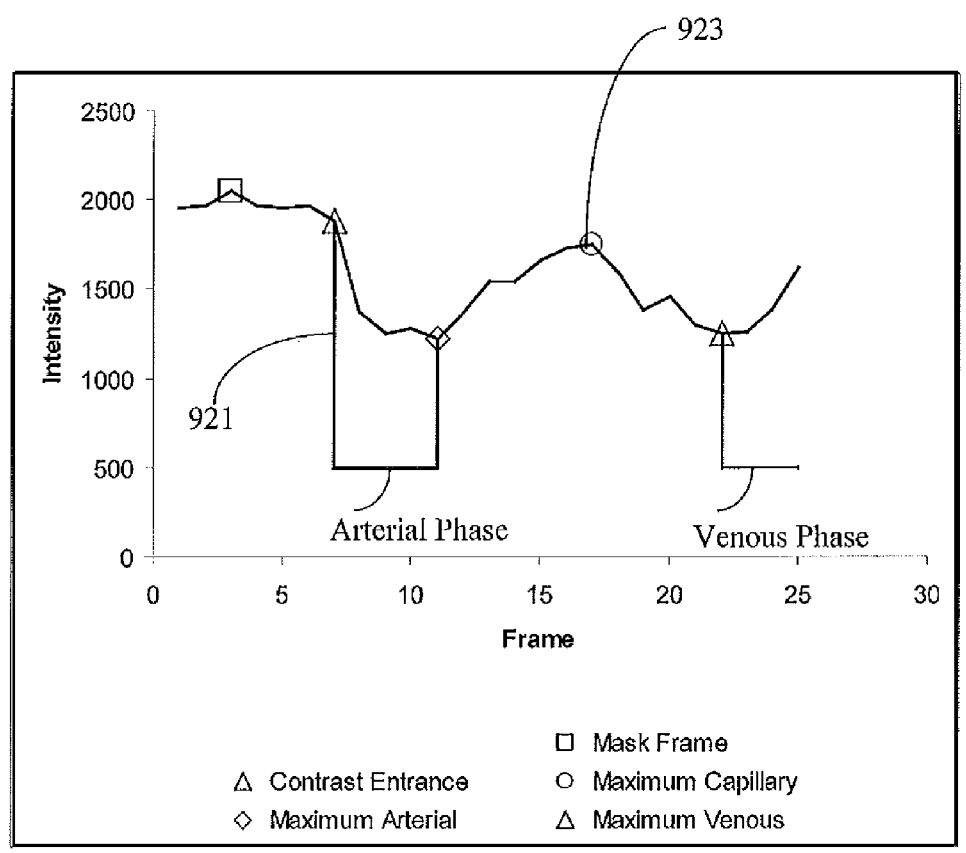
FIG. 11 illustrates arterial and venous phase transitions in the plot of minimum luminance intensity value for each frame of a sequence, according to invention principles.

FIG. 11 illustrates arterial and venous phase transitions in the plot of minimum luminance intensity value for each frame of a sequence. The start of the arterial phase is the first frame in the DSA image sequence which contains contrast agent. This is determined by system 10 (FIG. 6) from the minimum luminance intensity curve as the first frame (point 921) in the sequence (sequentially identified on the x-axis) having a minimum luminance intensity value more than 5% lower than the preceding frame lowest minimum luminance intensity of the sequence. The frame containing the maximum capillary blush (point 923) is determined by system 10 as the highest peak of the minimum intensity curve before the minimum luminance intensity returns to the pre-arterial intensity range. The maximum capillary blush is automatically detected by system 10 finding the first frame following the start of the arterial phase having a minimum luminance intensity value higher than the intensity value of the six closest frames (3 preceding and 3 subsequent frames). Other embodiments may employ different methods for finding the start of the arterial phase and the maximum capillary blush peak.

Figure 12:
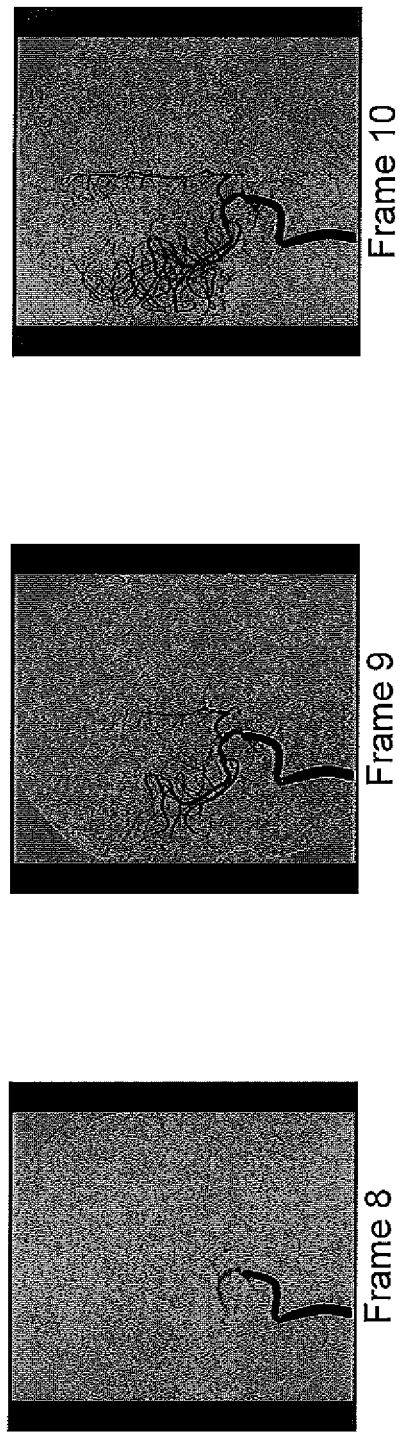
FIG. 12 comprises three frames (frames 8, 9, 10) showing increased lightness in shade in the internal carotid artery (largest artery at the bottom of the image) of frame 9 in comparison with frames 8 and 10, according to invention principles.

The end of the arterial phase is the lowest point on the curve between the start of the arterial phase and the maximum capillary blush frame. Different factors may influence the minimum luminance intensity value between the start of the arterial phase and the maximum capillary blush frame, so this value is variable and its determination is subject to a tolerance. The frame designating the end of the arterial phase is detected by system 10 finding the frame with the lowest luminance intensity between the start of the arterial phase and the maximum capillary blush frame or a subsequent frame (between the start of the arterial phase and the maximum capillary blush point) that is within 5% of the lowest luminance intensity value. There is a dip in the luminance intensity at frame 9, which is not the end of the arterial phase. In this example this dip in intensity is caused by a temporary reduction in the flow of contrast agent into the vessel. This is shown in image 9 of FIG. 12. Specifically, FIG. 12 comprises three frames (frames 8, 9, 10) showing increased lightness in shade in the internal carotid artery (largest artery at the bottom of the image) of frame 9 in comparison with frames 8 and 10.

The start of the venous phase is found by system 10 in a similar way as the end of the arterial phase by finding the frame with the lowest intensity between the maximum capillary blush frame and the last frame in the DSA image sequence or a preceding frame (between the maximum capillary blush and the last frame) that is within 5% of the lowest intensity. The end of the venous phase is determined by system 10 as the last frame in the image sequence having a minimum intensity value less than the lowest minimum intensity value of the pre-arterial frames. The DSA image sequence may not show complete washout of contrast agent and a venous frame may be the last frame of the DSA image sequence.

Figure 13:
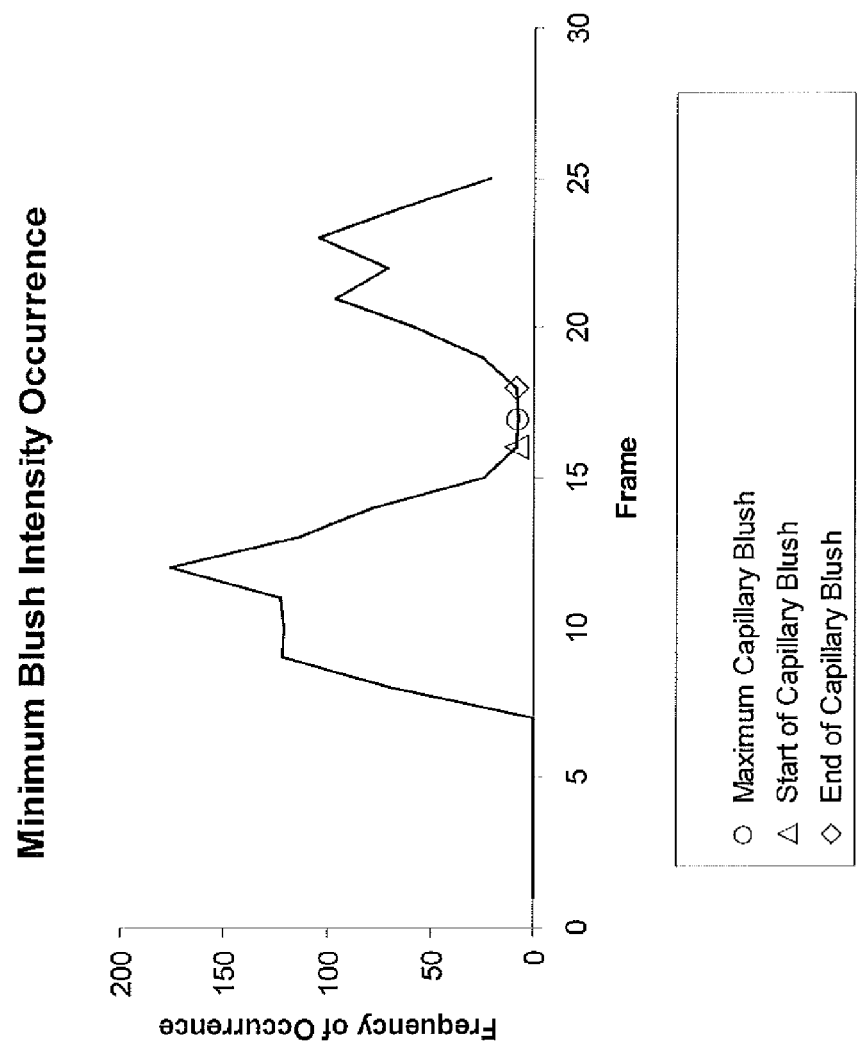
FIG. 13 shows a plot of the number of pixels containing a minimum intensity value for each frame of a DSA image sequence, according to invention principles.

FIG. 13 shows a plot generated by system 10 of the number of pixels (frequency of occurrence y-axis) containing the minimum intensity value for the maximum capillary blush image for each frame (with the frames being identified on the x-axis) in the image sequence. The capillary phase lies between the end of the arterial phase and the start of the venous phase, however multiple frames show a composite of blood (contrast agent) flow in arteries and veins together with the capillary blush. System 10 (FIG. 6) selects frames that show primarily the capillary blush using the minimum intensity value for the maximum capillary blush image and the FIG. 13 data. System 10 determines the frames that depict primarily the capillaries by identifying the frames in the FIG. 13 plot that have a frequency of occurrence (of the maximum blush minimum intensity value) near the frequency of occurrence for the maximum blush frame. System 10 automatically selects capillary frames by finding the frames having a frequency of occurrence less than twice that of the maximum capillary blush frame. Other embodiments may employ different methods for finding the extents of the capillary phase.

Figure 14:
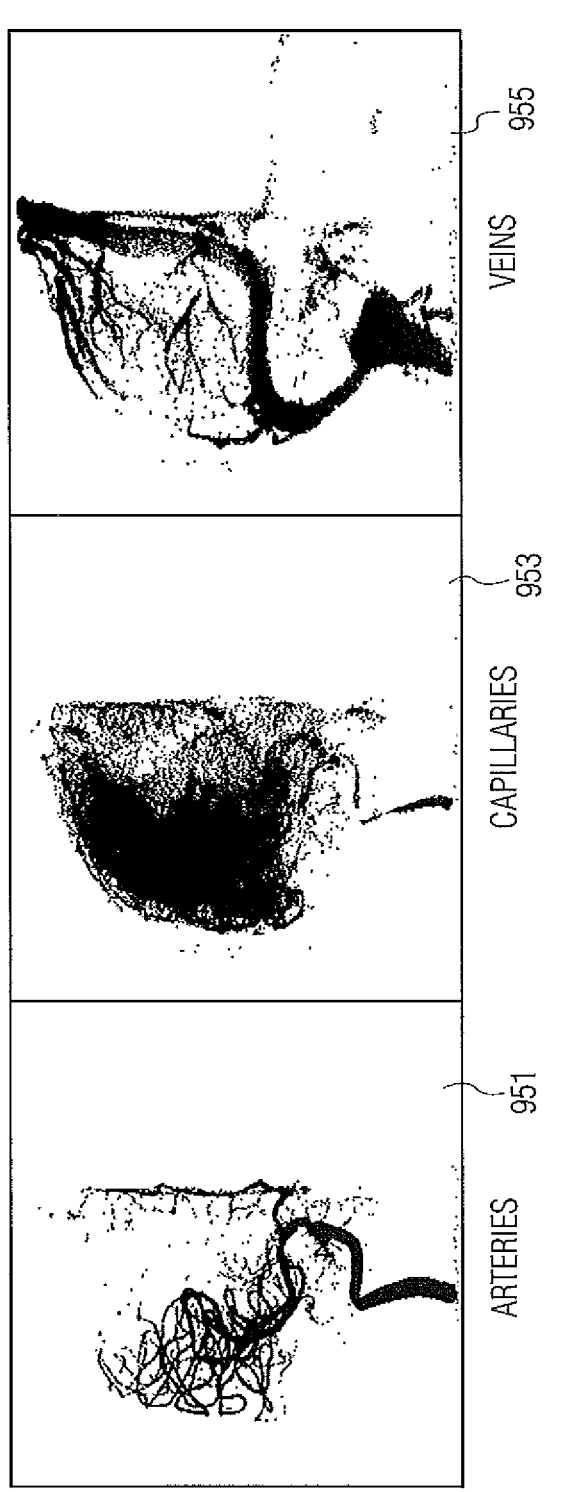
FIG. 14 shows individual images that show the arteries, capillaries, and veins generated by combining frames of each phase into a single image, according to invention principles.
Figure 15:
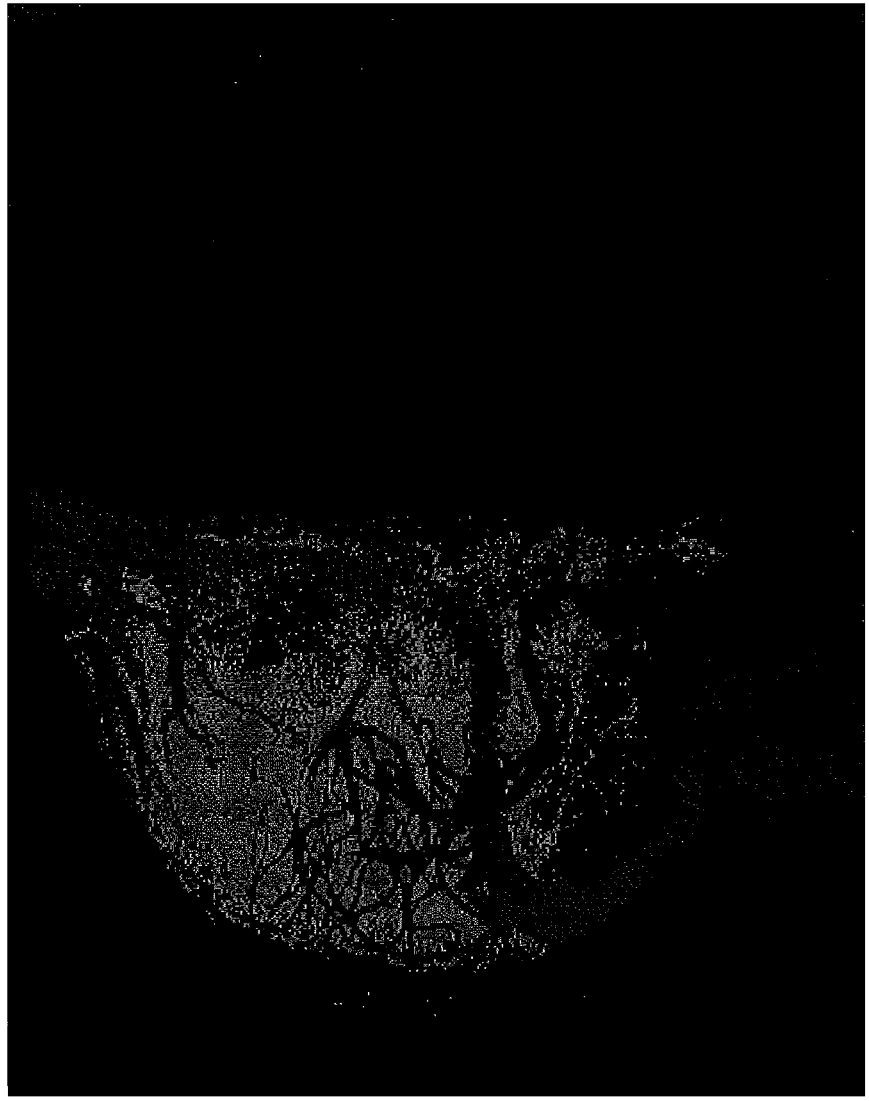
FIG. 15 shows an individual composite image that shows arteries, capillaries, and veins generated by combining frames of each phase into a single image, according to invention principles.
Figure 16:
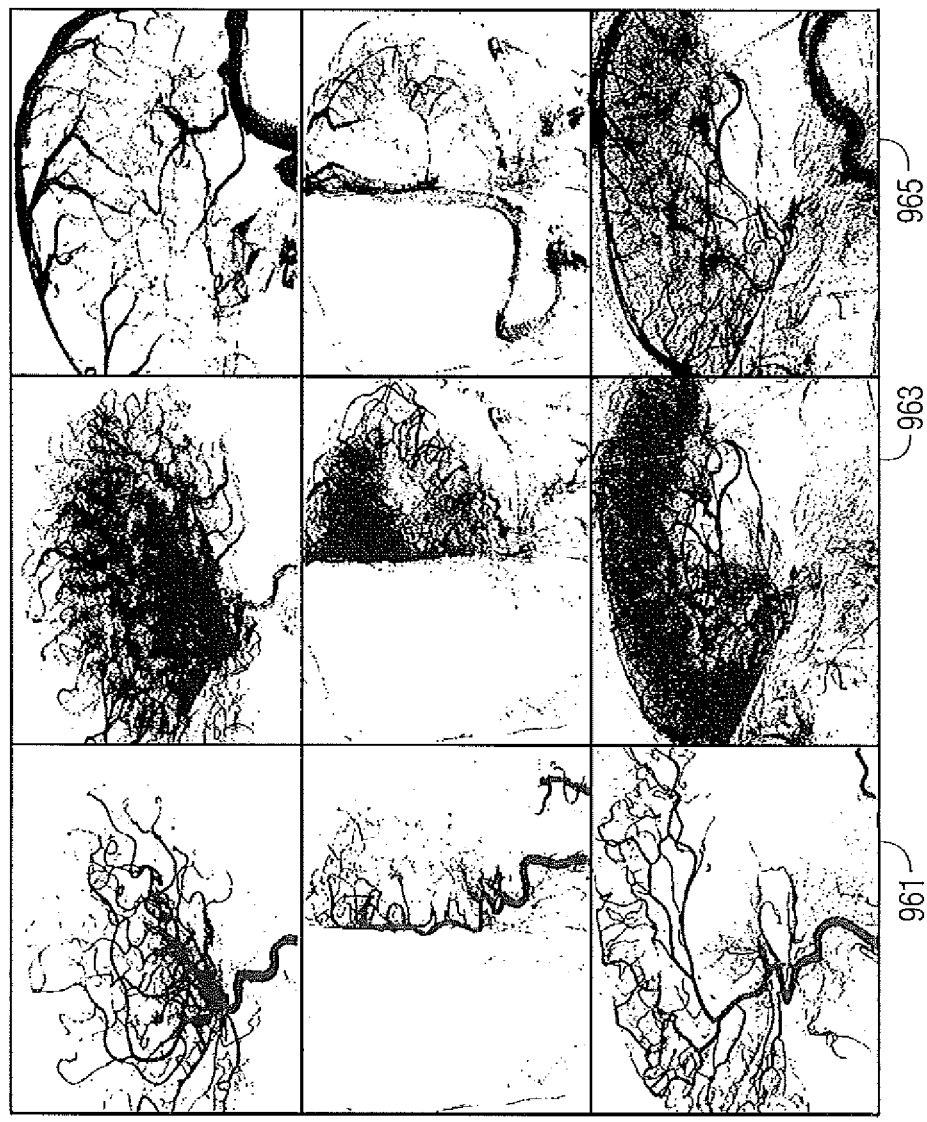
FIG. 16 shows additional vessel phase detection images from other DSA image sequences, according to invention principles.

System 10 identifies the frames of a DSA image sequence that primarily depict arteries, capillaries, and veins and identifies the frames of the DSA image sequence that contain a mixture of arteries and capillaries or a mixture of capillaries and veins. System 10 generates individual images that show the arteries, capillaries, and veins by combining frames of each phase into a single image. Specifically, FIG. 14 shows individual images that show the arteries, capillaries, and veins generated by system 10 by, combining frames in an arterial phase to provide composite arterial phase image 951, combining frames in a capillary phase to provide composite capillary phase image 953 and combining frames in a venous phase to provide composite venous phase image 955. FIG. 15 shows an individual composite image that show arteries, capillaries, and veins. System 10 generates the composite image of FIG. 15 by combining frames of each phase into a single image. FIG. 16 shows additional vessel phase detection images from other DSA image sequences showing arterial phase in column 961, capillary phase in column 963 and venous phase in column 65.

In artery, capillary, and vein mask images, there are some pixels that are included which do not belong to a vessel. These pixels are included due to a subtraction artifact produced by a difference between the mask and active frame resulting from patient movement (causing bone ghosting), image detector pixel errors, or noise, for example. Noise may be partially removed using a de-speckling operation (e.g., region shrinking and subsequent region growing constrained to regions of the original image) or a connectivity check. In addition to falsely identified pixels, images include under identified pixels. These are pixels that identify vessels and should be included, but have intensities that are within the range of the pre-fill phase intensities. These pixels may be re-incorporated by applying a region growing operation in a mask image to neighboring pixels having luminance intensities close to the intensities of adjacent marked pixels that are within the range of pre-fill phase intensities.

An image may include early (proximal) branching of a primary vessel that leads to early capillary phase being present during the arterial phase. In one embodiment, system 10 (FIG. 6) segments an image into smaller images and performs vessel segmentation analysis on the smaller images, combining the results into an overall vessel segmentation result for the entire image. Instead of, or in addition to, looking at minimum luminance intensity of the histogram of each frame in the DSA sequence, system 10 in one embodiment uses the frequency of occurrence of intensities of a capillary phase to find the maximum capillary blush frame as well as the frames that contain a higher percentage of capillary pixels relative to the number of artery or vein pixels.

In another embodiment, system 10 examines a derivative of a slope of a minimum luminance intensity curve. The derivative of the slope describes the change in the slope at each frame. The frames where the slope changes polarity indicate an inflection point in the minimum luminance intensity curve. These inflection point are used to determine end of an arterial phase, start of a capillary phase, end of a capillary phase, or start of a venous phase. This method may be susceptible to fluctuations in the minimum luminance intensity curve due to noise, contrast bolus geometry variation, and patient movement. An image data processing system automatically uses the previously described methods to detect vessel phase associated with each frame within a digitally subtracted angiography (DSA) image to classify each frame as, arterial, venous, capillary, or mixed phase. An interface acquires a sequence of images of patient vessels both prior to and following introduction of positive contrast agent into the vessels and subtracts a mask image representing background detail in the absence of a contrast agent to produce data representing a sequence of digitally subtracted images enhancing vessel structure.

An image data processor determines individual minimum luminance intensity level values of corresponding individual images (frames) of the sequence to automatically identify an image in the sequence substantially corresponding to at least one of (a) a first transition into the arterial phase of blood flow in response to identifying a first image in the sequence having a plurality of pixels with a minimum luminance intensity level lower than a minimum background threshold level, (b) a first position within the capillary phase of blood flow, the maximum capillary blush, in response to identifying an image in the sequence following the first transition in the sequence having a maximum of the minimum luminance intensity level values, (c) a second transition out of the arterial phase of blood flow in response to identifying an image in the sequence following the first transition and preceding the first position in the sequence having a minimum of the minimum luminance intensity level values, (d) a third transition into the venous phase of blood flow in response to identifying an image in the sequence following the first position in the sequence having a minimum of the minimum luminance intensity level values, (e) a fourth transition out of the venous phase of blood flow in response to identifying an image in the sequence following the third transition in the sequence having a plurality of pixels with a minimum luminance intensity level higher than the same minimum background threshold level value used to detect the first transition.

The capillary frames are identified by, 1) finding the minimum luminance intensity level present in a maximum capillary blush frame and 2) finding the number of times that the capillary blush minimum luminance intensity level occurs in each frame in a DSA sequence. In one embodiment, the minimum luminance intensity level is the lowest luminance intensity level that occurs 5 or more times in the maximum capillary blush frame, for example (the capillary blush minimum luminance intensity). The capillary frames are frames having a count of the capillary blush minimum luminance intensity level near (within a tolerance of) the count of the capillary blush minimum luminance intensity for the maximum capillary blush frame. The tolerance may be either (a) a fixed value, or (b) a multiplier of the count of the capillary blush minimum luminance intensity for the maximum capillary blush frame.

In a DSA image sequence, a transition into a capillary phase is the first frame in the sequence that is identified by system 10 as a capillary frame. Similarly, the transition out of the capillary phase is the last frame in the sequence that is identified by system 10 as a capillary frame. Not all frames in the sequence need to be evaluated to determine the capillary frames, and evaluation of frames to identify capillary frames is performed sequentially on the frames preceding and following the maximum capillary blush frame, starting with frames closest to the maximum capillary blush frame and extending in each direction (before and after the maximum capillary blush frame). An output processor automatically assigns an attribute to image data to identify vessel phase in response to identifying different transitions in data derived from image data of a DSA image sequence. A minimum background threshold level is selected as one of a plurality of fixed values established through system calibration or evaluation to be a lowest expected luminance intensity level introduced by noise and/or scatter for a DSA image of particular patient anatomy of a patient with specific biometrics. Further, an image in the DSA sequence in FIG. 11 is selected as a first transition by system 10 as having a minimum luminance intensity level higher than the minimum luminance intensity level of a plurality of preceding and following images in the DSA sequence. The plurality of preceding and following images comprise a minimum number of images to reduce impact of image noise, contrast injection bolus inconsistency, or patient movement. The minimum number of images comprises at least five images (the image being investigated as well as the 2 images preceding and 2 images following). The minimum of the minimum luminance intensity level values for computing a second transition in FIG. 11 is selected as the image in the DSA sequence having the lowest minimum luminance intensity level in the range of images in the DSA sequence, between the first transition and a first position.

The minimum of the minimum luminance intensity level values for computing the second transition is selected as the image in the DSA sequence closest to the first position having a minimum luminance intensity level within a specified tolerance of the lowest minimum luminance intensity level in the range of images in the DSA sequence, between the first transition and the first position. The specified tolerance is a percentage of the lowest luminance intensity level in the range. The minimum of the minimum luminance intensity level values for computing a third transition in FIG. 11 is selected as an image in the DSA sequence having the lowest minimum luminance intensity level in the range of images in the DSA sequence, between the first position and a fourth transition. The minimum of the minimum luminance intensity level values for computing the third transition is selected as the image in the DSA sequence closest to a first position having a minimum luminance intensity level within a specified tolerance of the lowest minimum luminance intensity level in the range of images in the DSA sequence.

The image data processor identifies a plurality of images in the sequence as substantially exclusively displaying arteries, comprising the range of images between the first and second transitions, inclusively. The image data processor identifies a plurality of images in the sequence as substantially exclusively displaying veins, comprising the range of images between identified transitions. The image data processor identifies a plurality of images in the sequence as substantially exclusively displaying capillaries, comprising the range of images between identified transitions, inclusively. The image data processor identifies a plurality of images in the sequence as displaying a combination of arteries and capillaries, comprising the range of images between identified transitions, inclusively. The image data processor identifies a plurality of images in the sequence as displaying a combination of capillaries and veins, comprising the range of images between identified transitions, inclusively.

Figure 17:
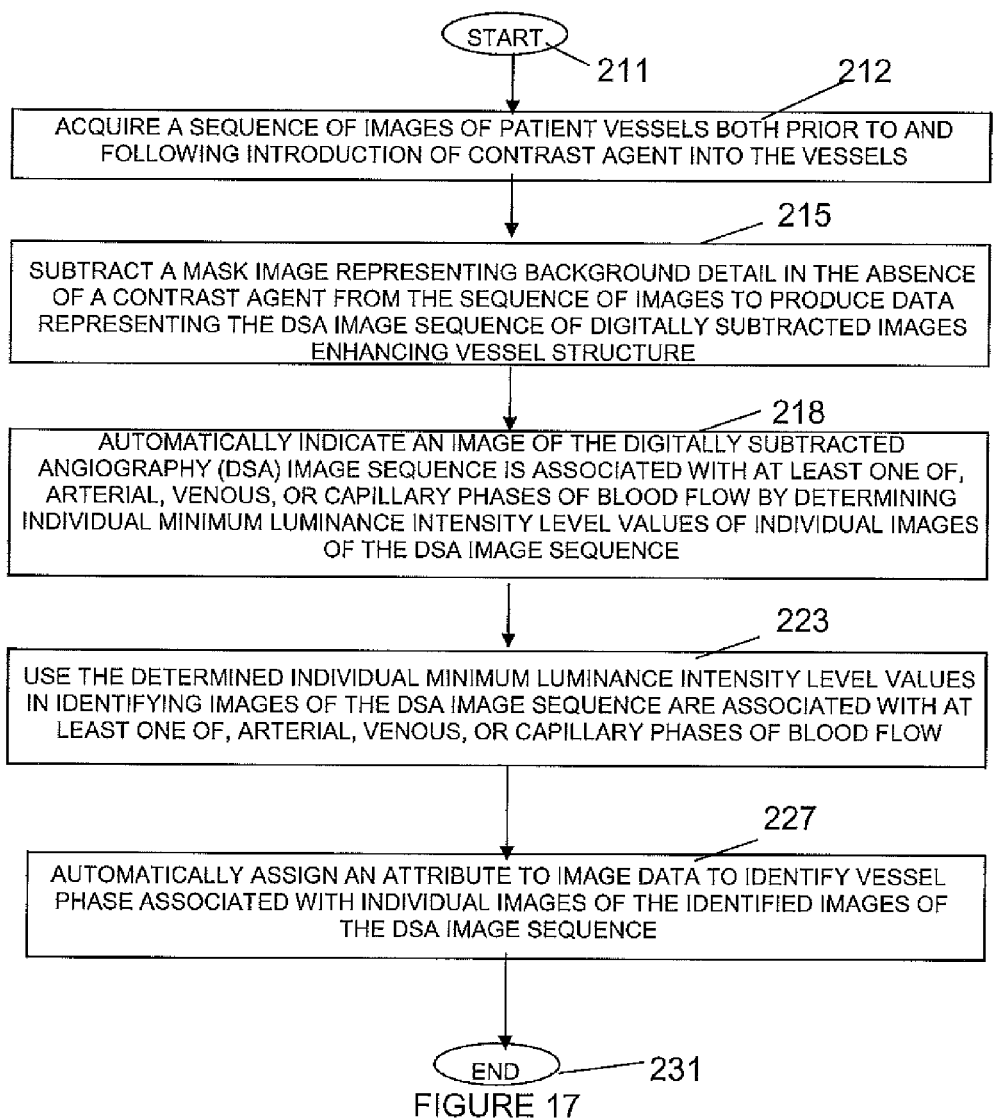
FIG. 17 shows a flowchart of a process used by an image data processing system for automatically indicating an image of a digitally subtracted Angiography (DSA) image sequence is associated with at least one of, arterial, venous, or capillary phases of blood flow, according to invention principles.

FIG. 17 shows a flowchart of a process used by image data processing system 10 for automatically indicating an image of a digitally subtracted Angiography (DSA) image sequence is associated with at least one of, arterial, venous, or capillary phases of blood flow. In step 212, following the start at step 211, interface 23 acquires a sequence of images of patient vessels both prior to and following introduction of contrast agent into the vessels. In step 215 interface 23 subtracts a mask image representing background detail in the absence of a contrast agent from the sequence of images to produce data representing the DSA image sequence of digitally subtracted images enhancing vessel structure.

In step 218 image data processor 15 automatically indicates an image of the DSA image sequence is associated with at least one of, arterial, venous, or capillary phases of blood flow by determining individual minimum luminance intensity level values of individual images of the DSA image sequence. Processor 15 in step 223 uses the determined individual minimum luminance intensity level values in identifying images of the DSA image sequence are associated with at least one of, arterial, venous, or capillary phases of blood flow. Image data processor 15 uses the determined individual minimum luminance intensity level values to automatically identify an image in the DSA sequence substantially corresponding to a first transition to an arterial phase of blood flow in response to identifying a first image in the DSA sequence having multiple pixels with a minimum luminance intensity level lower than a threshold level associated with a background luminance intensity level. The multiple pixels comprise a minimum number of pixels (at least four pixels) to reduce impact of noise. The background luminance intensity level substantially comprises a minimum luminance intensity level associated with a mask image. The threshold level is selected as a luminance intensity level lower than the lowest minimum luminance intensity level of the image in the sequence acquired prior to the introduction of the contrast agent into the vessels.

Image data processor 15 uses the determined individual minimum luminance intensity level values to automatically identify an image in the DSA sequence substantially corresponding to a maximum capillary blush image having a maximum of the minimum luminance intensity level values following the image in the DSA sequence substantially corresponding to the first transition. Image data processor 15, identifies a range of the minimum luminance intensity level values associated with the maximum capillary blush image and identifies multiple images in the DSA sequence associated with contrast agent flow substantially exclusively into capillaries in response to the identified range. The identified range of the minimum luminance intensity level values comprises a proportion of the maximum of the minimum luminance intensity level values of maximum capillary blush image. The proportion of the maximum of the minimum luminance intensity level values comprises at least one of, (a) a predetermined proportion and (b) a proportion determined based on a determined rate of contrast agent flow in the anatomy of the patient.

Image data processor 15 identifies multiple images in the DSA sequence as substantially exclusively displaying arteries, comprising images in the DSA sequence following the first transition up to, and exclusive of, a first capillary phase image. Processor 15 further identifies multiple images in the DSA sequence as substantially displaying arteries, comprising images between the first transition and an image in the DSA sequence associated with start of the contrast agent flow into the capillaries. Image data processor also identifies multiple images in the DSA sequence as substantially exclusively displaying veins comprising images following the image in the DSA sequence associated with end of the contrast agent flow in the capillaries and start of a new arterial phase. Further, image data processor 15 identifies multiple images in the DSA sequence as substantially exclusively displaying veins comprising images following an image in the DSA sequence associated with end of the contrast agent flow in the capillaries and start of a new arterial phase.

Image data processor 15 automatically identifies an image transition from the first phase comprising an arterial phase of blood flow to a second phase comprising a capillary phase and automatically identifies an image transition from the second phase comprising a capillary phase of blood flow to a third phase comprising a venous phase. Image data processor 15 automatically allocates different visual attributes to identify blood flow in an image associated with at least one of, arterial, capillary and venous phase. The image data different visual attributes comprise at least one of different colors, different shading, different highlighting, different background and different foreground. Further, in an inverted luminance configuration, image data processor 15 determines and uses individual maximum luminance intensity level values to automatically identify an image in the DSA sequence substantially corresponding to a first transition to an arterial phase of blood flow in response to identifying a first image in the DSA image sequence having multiple pixels with a maximum luminance intensity level lower than a threshold level associated with a background luminance intensity level.

In step 227, output processor 29 automatically assigns an attribute to image data to identify vessel phase associated with individual images of the identified images of the DSA image sequence. Output processor 29 automatically generates individual images and a single composite image that separately identifies the arteries, capillaries, and veins. Output processor 29 further automatically generates a single composite image that identifies two or more of, artery, capillary, and vein vessel phases.

Image data processor 15 uses the determined individual minimum luminance intensity level values to automatically identify an image in the DSA sequence substantially corresponding to the end of the arterial phase of blood flow in response to identifying the image in the DSA sequence having a minimum luminance intensity level value comprising a minimum of the minimum luminance intensity level values in the DSA sequence following the image in the DSA sequence substantially corresponding to the start of the arterial phase and preceding the image in the DSA sequence substantially corresponding to the maximum capillary blush image. Image data processor 15 also uses the determined individual minimum luminance intensity level values to automatically identify an image in the DSA sequence substantially corresponding to the end of the venous phase of blood flow in response to identifying a first image in the DSA sequence having a plurality of pixels with a minimum luminance intensity level above a threshold level associated with a background luminance intensity level following the image in the DSA sequence substantially corresponding to the maximum capillary blush image. The background luminance intensity level substantially comprises a minimum luminance intensity level associated with a mask image. Further, the threshold level is selected as a luminance intensity level lower than the lowest minimum luminance intensity level of the image in the sequence acquired prior to introduction of the contrast agent into the vessels.

Image data processor 15 uses the determined individual minimum luminance intensity level values to automatically identify an image in the DSA sequence substantially corresponding to the start of the venous phase of blood flow in response to identifying an image in the DSA sequence having a plurality of pixels with a minimum luminance intensity level that is the lowest minimum luminance intensity level in the DSA sequence following the image in the DSA sequence substantially corresponding to the maximum capillary blush image and preceding the image in the DSA sequence substantially corresponding to the end of the venous phase. The process of FIG. 17 terminates at step 231.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 3-17 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system provides automatic detection and classification of the vessels as arteries, veins, and capillaries within a DSA image sequence and displays classified vessels, in response to a contrast agent bolus injection into a patient and analyzes the change in image luminance intensity values over time to identify frames that specifically capture contrast agent as it moves through arteries, capillaries, and veins. Further, the processes and applications may, in alternative embodiments, be located on one or more (e.g., distributed) processing devices on a network linking the units of FIG. 6. Any of the functions and steps provided in FIGS. 3-17 may be implemented in hardware, software or a combination of both.

What is claimed is:

1. An image data processing system, comprising:
an interface for acquiring a sequence of images of patient vessels both prior to and following introduction of contrast agent into the vessels and for subtracting a mask image representing background detail in the absence of a contrast agent to produce data representing a DSA sequence of digitally subtracted images enhancing vessel structure;
an image data processor for determining individual minimum luminance intensity level values of individual images of said DSA sequence and using the determined individual minimum luminance intensity level values to determine that a first one or more of the individual images of said DSA sequence depicts an arterial phase of blood flow, that a second one or more of the individual images of said DSA sequence depicts a venous phase of blood flow, and that a third one or more of the individual images of said DSA sequence depicts a capillary phase of blood flow; and
an output processor for automatically assigning an attribute to each of the individual images of said DSA sequence to identify a vessel phase depicted by the individual images of said DSA sequence.

2. A system according to claim 1, wherein
said image data processor identifies a plurality of images in said DSA sequence as substantially displaying arteries, comprising images between the start of the arterial phase image and an image in said DSA sequence associated with start of said contrast agent flow into said capillaries.

3. A system according to claim 1, wherein
said image data processor identifies a plurality of images in said DSA sequence as substantially displaying veins comprising images following an image in said DSA sequence associated with end of said contrast agent flow in said capillaries and preceding start of a new arterial phase.

4. A system according to claim 1, wherein
said output processor automatically generates either individual images or a single composite image that separately identifies the arteries, capillaries, and veins.

5. A system according to claim 1, wherein
said image data processor automatically identifies an image transition from said first phase comprising an arterial phase of blood flow to a second phase comprising a capillary phase and
said image data processor automatically identifies an image transition from said second phase comprising a capillary phase of blood flow to a third phase comprising a venous phase.

6. A system according to claim 1, wherein
said image data processor automatically allocates different visual attributes to identify blood flow in an image associated with arterial, capillary and venous phase.

7. A system according to claim 6, wherein
the image data different visual attributes comprise at least one of different colors, different shading, different highlighting, different background and different foreground.

8. A system according to claim 1, wherein
said image data processor automatically allocates different visual attributes to identify blood flow in an image associated with at least two of arterial, capillary and venous phases and
the image data different visual attributes comprise at least one of different colors, different shading, different highlighting, different background and different foreground.

9. A system according to claim 1, wherein
in an inverted luminance configuration,
said image data processor determines and uses individual maximum luminance intensity level values to determine that an image in said DSA sequence depicting a first transition to an arterial phase of blood flow by identifying a first image in said DSA sequence having a plurality of pixels with a maximum luminance intensity level lower than a threshold level associated with a background luminance intensity level.

10. A system according to claim 1, wherein
said output processor automatically generates a single composite image that identifies two or more of, artery, capillary, and vein vessel phases.

11. A system according to claim 1, wherein
said DSA sequence comprises a two dimensional (2D) or a three dimensional (3D) DSA image sequence.

12. A system according to claim 1, wherein
said minimum luminance intensity level comprises a maximum luminance intensity level for a negative contrast agent.

13. A system according to claim 1, wherein
said image data processor uses the determined individual minimum luminance intensity level values to determine that an image in said DSA sequence depicts a start of an arterial phase of blood flow by identifying a first image in said DSA sequence having a plurality of pixels with a minimum luminance intensity level lower than a threshold level associated with a background luminance intensity level.

14. A system according to claim 13, wherein
said background luminance intensity level substantially comprises a minimum luminance intensity level associated with a mask image.

15. A system according to claim 13, wherein
said threshold level is selected as a luminance intensity level lower than the lowest minimum luminance intensity level of the image in said sequence acquired prior to said introduction of said contrast agent into the vessels.

16. A system according to claim 13, wherein
said image data processor uses the determined individual minimum luminance intensity level values to determine that an image in said DSA sequence is a maximum capillary blush image having a maximum of said minimum luminance intensity level values of images following said image in said DSA sequence depicting said start of an arterial phase of blood flow.

17. A system according to claim 16, wherein
said image data processor,
identifies a range of said minimum luminance intensity level values associated with said maximum capillary blush image and
identifies a plurality of images in said DSA sequence associated with contrast agent flow substantially exclusively into capillaries in response to the identified range.

18. A system according to claim 17, wherein
the identified range of said minimum luminance intensity level values comprises a proportion of said minimum luminance intensity level value of the maximum capillary blush image.

19. A system according to claim 18, wherein
said proportion of the maximum of said minimum luminance intensity level values comprises at least one of, (a) a predetermined proportion and (b) a proportion determined based on a determined rate of contrast agent flow in the anatomy of the patient.

20. A system according to claim 16, wherein
said image data processor,
identifies a number of pixels having said minimum luminance intensity level value associated with said maximum capillary blush image and
identifies a plurality of images in said DSA sequence associated with contrast agent flow substantially exclusively into capillaries in response to the identified number of pixels.

21. A system according to claim 20, wherein
the identified plurality of images in said DSA sequence comprises images having a predetermined proportion of a frequency of occurrence of pixels having said minimum luminance intensity level value of said maximum capillary blush image.

22. A system according to claim 16, wherein
said image data processor uses the determined individual minimum luminance intensity level values to determine that an image in said DSA sequence depicts an end of the arterial phase of blood flow by identifying an image in said DSA sequence having a minimum luminance intensity level value comprising a minimum of said minimum luminance intensity level values in said DSA sequence of images following said image in said DSA sequence depicting the start of the arterial phase and preceding said maximum capillary blush image.

23. A system according to claim 22, wherein
said image data processor identifies a plurality of images in said DSA sequence as substantially exclusively displaying arteries, comprising images in said DSA sequence following said start of the arterial phase image up to, and inclusive of, the end of the arterial phase image.

24. A system according to claim 16, wherein
said image data processor uses the determined individual minimum luminance intensity level values to determine that an image in said DSA sequence depicts an end of the venous phase of blood flow by identifying a first image in said DSA sequence having a plurality of pixels with a minimum luminance intensity level above a threshold level associated with a background luminance intensity level of images following said image in said maximum capillary blush image.

25. A system according to claim 24, wherein
said background luminance intensity level substantially comprises a minimum luminance intensity level associated with a mask image.

26. A system according to claim 24, wherein
said threshold level is selected as a luminance intensity level lower than the lowest minimum luminance intensity level of the image in said sequence acquired prior to introduction of said contrast agent into the vessels.

27. A system according to claim 24, wherein
said image data processor uses the determined individual minimum luminance intensity level values to determine that an image in said DSA sequence depicts a start of the venous phase of blood flow by identifying an image in said DSA sequence having a plurality of pixels with a minimum luminance intensity level that is the lowest minimum luminance intensity level of images in said DSA sequence following said maximum capillary blush image and preceding said image in said DSA sequence depicting the end of the venous phase.

28. A system according to claim 24, wherein
said image data processor identifies a plurality of images in said DSA sequence as substantially exclusively displaying veins comprising images following said image in said DSA sequence associated with the start of the venous phase and preceding, the image in said DSA sequence associated with the end of the venous phase.

29. A system according to claim 13, wherein
said plurality of pixels comprise a minimum number of pixels to reduce impact of noise.

30. A system according to claim 29, wherein
said minimum number of pixels comprises at least four pixels.

31. An image data processing method comprising:
determining individual minimum luminance intensity level values of individual images of the DSA image sequence;
using the determined individual minimum luminance intensity level values to determine that a first one or more of the individual images of said DSA image sequence depicts an arterial phase of blood flow, that a second one or more of the individual images of said DSA sequence depicts a venous phase of blood flow, and that a third one or more of the individual images of said DSA sequence depicts a capillary phase of blood flow; and
automatically assigning an attribute to each of the individual images of said DSA sequence to identify a vessel phase depicted by the individual images of said DSA image sequence.

32. A method according to claim 31, including the activities of
acquiring a sequence of images of patient vessels both prior to and following introduction of contrast agent into the vessels and
subtracting a mask image representing background detail in the absence of a contrast agent from said sequence of images to produce data representing said DSA image sequence of digitally subtracted images enhancing vessel structure;
automatically indicating an image of said digitally subtracted Angiography (DSA) image sequence depicts at least one of, arterial, venous, or capillary phases of blood flow.

33. A method according to claim 31, comprising:
determining, based on the determined individual minimum luminance intensity level values, that a first image in said DSA image sequence depicts a start of arterial blood flow and includes a plurality of pixels with a minimum luminance intensity level lower than a threshold level associated with a background luminance intensity level.

34. A non-transitory storage medium of machine readable instructions executable to:
determine individual minimum luminance intensity level values of individual images of the DSA image sequence;
using the determined individual minimum luminance intensity level values to determine that a first one or more of the individual images of said DSA image sequence depicts an arterial phase of blood flow, that a second one or more of the individual images of said DSA sequence depicts a venous phase of blood flow, and that a third one or more of the individual images of said DSA sequence depicts a capillary phase of blood flow; and
automatically assigning an attribute to each of the individual images of said DSA sequence to identify a vessel phase depicted by the individual images of said DSA image sequence.

\* \* \* \* \*